US00PP20211P2

(12) United States Plant Patent
Arts

(10) Patent No.: US PP20,211 P2
(45) Date of Patent: Aug. 11, 2009

(54) POINSETTIA PLANT NAMED 'STARGAZER WHITE'

(50) Latin Name: ***Euphorbia pulcherrima* Willd.**
Varietal Denomination: Stargazer White

(75) Inventor: Niels Arts, De Kwakel (NL)

(73) Assignee: Agriom B.V., De Kwakel (NL)

( * ) Notice: Subject to any disclaimer, the term of this patent is extended or adjusted under 35 U.S.C. 154(b) by 0 days.

(21) Appl. No.: 12/214,228

(22) Filed: Jun. 16, 2008

(51) Int. Cl.
*A01H 5/00* (2006.01)

(52) U.S. Cl. ..... Plt./304

(58) Field of Classification Search ..... Plt./304
See application file for complete search history.

(56) References Cited

PUBLICATIONS

Upov Plant Variety Database 2008/5 p. 1.*

* cited by examiner

*Primary Examiner*—Annette H Para
(74) *Attorney, Agent, or Firm*—C. A. Whealy

(57) ABSTRACT

A new and distinct cultivar of Poinsettia plant named 'Stargazer White', characterized by its uniform, strong, upright and mounded plant habit; freely branching habit; dark green-colored leaves; early flowering response; large inflorescences with creamy white-colored flower bracts; and excellent post-production longevity.

1 Drawing Sheet

Botanical designation: *Euphorbia pulcherrima* Willd.
Cultivar denomination: 'STARGAZER WHITE'.
Referenced to related applications: Title: Poinsettia Plant Named 'Stargazer Marble'. Applicant: Niels Arts. Plant patent application Ser. No. 12/214,231.

BACKGROUND OF THE INVENTION

The present invention relates to a new and distinct cultivar of Poinsettia plant, botanically known as *Euphorbia pulcherrima* Willd., and hereinafter referred to by the name 'Stargazer White'.

The new Poinsettia is a naturally-occurring whole plant mutation of *Euphorbia pulcherrima* Willd. 'Stargazer', disclosed in U.S. Plant Pat. No. 17,022. The new Poinsettia was discovered and selected by the Inventor as a flowering plant within a population of plants of 'Stargazer' in a controlled greenhouse environment in Aalsmeer, The Netherlands in May, 2004.

Asexual reproduction of the new Poinsettia by terminal vegetative cuttings propagated in a controlled greenhouse environment in Aalsmeer, The Netherlands since July, 2004, has shown that the unique features of this new Poinsettia are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Stargazer White'. These characteristics in combination distinguish 'Stargazer White' as a new and distinct cultivar of Poinsettia:

1. Uniform, strong, upright and mounded plant habit.
2. Freely branching habit.
3. Dark green-colored leaves.
4. Early flowering response.
5. Large inflorescences with creamy white-colored flower bracts.
6. Excellent post-production longevity.

In side-by-side comparisons conducted in Aalsmeer, The Netherlands, plants of the new Poinsettia differed from plants of 'Stargazer' primarily in flower bract color as plants of 'Stargazer' have dark red-colored flower bracts.

Plants of the new Poinsettia can be compared to plants of the *Euphorbia pulcherrima* Willd. 'Stargazer Marble', disclosed in a U.S. Plant patent application Ser. No. 12/214,231. Plants of the new Poinsettia and 'Stargazer Marble' differ primarily in flower bract color as plants of 'Stargazer Marble' have creamy white and pink bi-colored flower bracts.

Plants of the new Poinsettia can be compared to plants of *Euphorbia pulcherrima* Willd. 'Fiscor', disclosed in U.S. Plant Pat. No. 9,364. In side-by-side comparisons conducted in Aalsmeer, The Netherlands, plants of the new Poinsettia differed from plants of 'Fiscor' in the following characteristics:

1. Plants of the new Poinsettia were stronger than plants of 'Fiscor'.
2. Plants of the new Poinsettia and 'Fiscor' differed in flower bract color as plants of 'Fiscor' have red-colored flower bracts.
3. Plants of the new Poinsettia had longer postproduction longevity than plants of 'Fiscor'.
4. Plants of the new Poinsettia were more cold tolerant than plants of 'Fiscor'.

BRIEF DESCRIPTION OF THE PHOTOGRAPH

The accompanying photograph illustrates the overall appearance of the new Poinsettia. The photograph shows the colors as true as it is reasonably possible to obtain in colored reproductions of this type. Colors in the photograph may differ slightly from the color values cited in the detailed botanical description which accurately describe the colors of the new Poinsettia. The photograph comprises a top perspective view of a typical flowering plant of 'Stargazer White'.

DETAILED BOTANICAL DESCRIPTION

Plants used for the aforementioned photograph and following observations and measurements were grown in 13-cm containers in De Kwakel, The Netherlands during the autumn and winter in a glass-covered greenhouse and under conditions and cultural practices which approximate those generally used in commercial Poinsettia production. During the first ten weeks of production of the plants, day and night temperatures averaged 20° C. and during the finishing production phase, day and night temperatures averaged 17° C. Light levels throughout the entire production period were about 200 Watts per square meter. Plants were pinched one time and were forced into flower under short day/long night photoperiodic conditions. Plants were 18 weeks from planting when the photograph and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'Stargazer White'.

Parentage: Naturally-occurring whole plant mutation of *Euphorbia pulcherrima* Willd. 'Stargazer', disclosed in U.S. Plant Pat. No. 17,022.

Propagation:

*Type.*—Terminal vegetative cuttings.

*Time to initiate roots.*—About 10 to 14 days at 22° C.

*Time to produce a rooted young plant.*—About four weeks at 22° C.

*Root description.*—Fibrous, medium to thick; white in color.

*Rooting habit.*—Freely branching; moderately dense.

Plant description:

*Plant habit and form.*—Uniform, strong, upright and mounded plant habit; inverted triangle. Inflorescences positioned above the foliar plane. Vigorous growth habit.

*Plant height.*—About 25 cm.

*Plant diameter or spread.*—About 30 cm.

*Lateral branch description.*—Quantity: Freely branching habit, about five lateral branches develop after pinching. Length: About 12 cm to 16 cm. Diameter: About 4 mm to 6 mm. Internode length: About 0.5 cm to 1.5 cm. Strength: Strong. Texture: Smooth, glabrous. Color: Close to 141D.

*Foliage description.*—Arrangement: Alternate, simple. Length: About 11 cm. Width: About 8 cm. Shape: Ovate. Apex: Acute. Base: Cuneate to obtuse. Margin: Entire or lobed. Venation pattern: Pinnate. Texture, upper and lower surfaces: Smooth, glabrous. Color: Developing foliage, upper surface: Close to 144A. Developing foliage, lower surface: Close to 144B. Fully expanded foliage, upper surface: Close to 137A; venation, close to 144A. Fully expanded foliage, lower surface: Close to 137C; venation, close to 144B. Petiole: Length: About 6.5 cm. Diameter: About 2 mm. Texture, upper and lower surfaces: Smooth, glabrous. Color, upper and lower surfaces: Close to 144A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Early flowering response, plants begin flowering about seven weeks after the start of short daylong day photoperiodic treatments.

*Post-production longevity.*—Excellent post-production longevity; plants of the new Poinsettia maintain good substance and bract color for about six weeks under interior conditions and for about eight weeks in the greenhouse.

*Inflorescence size.*—Diameter: About 21 cm. Height (depth): About 5 cm.

*Flower bracts.*—Quantity per inflorescence: About 12. Length, largest bracts: About 10 cm. Width, largest bracts: About 6 cm. Shape: Ovate. Apex: Acuminate. Base: Obtuse. Margin: Entire. Texture, upper and lower surfaces: Smooth, glabrous. Venation pattern: Pinnate. Color: Developing or transitional bracts, upper and lower surfaces: Close to 1D. Fully developed bracts, upper and lower surfaces: Close to 1D. Venation, upper and lower surfaces: Close to 1D. Bract petiole: Length: About 2 cm to 3 cm. Diameter: About 2 mm. Texture, upper and lower surfaces: Smooth, glabrous. Color, upper and lower surfaces: Close to 144A.

*Cyathia.*—Quantity per corymb: About five. Diameter of cyathia cluster: About 1.5 cm to 2 cm. Length: About 1 cm. Width: About 5 mm. Shape: Oval. Color, immature: Close to 154A. Color, mature: Close to 3A. Nectaries: Quantity per cyathium: Usually one. Size: About 5 mm. Color: Close to 24B.

*Peduncles.*—Length: About 5 mm. Diameter: About 5 mm. Strength: Strong. Aspect: Upright. Texture: Smooth, glabrous. Color: Close to 143A tinted with close to 185B.

*Reproductive organs.*—Stamens: Quantity per cyathium: About eight. Anther shape: Rounded. Anther length: About 0.5 mm. Anther color: Close to 14A. Amount of pollen: Abundant. Pollen color: Close to 12A. Pistils: Quantity per cyathium: About three. Pistil length: About 5 mm. Style length: About 2 mm. Style color: Close to 1D. Stigma shape: "V"-shaped. Stigma color: Close to 1D. Ovary color: Close to 143A.

*Seed/fruit.*—Seed and fruit development have not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 17° C. to about 35° C.

It is claimed:

1. A new and distinct Poinsettia plant named 'Stargazer White' as illustrated and described.

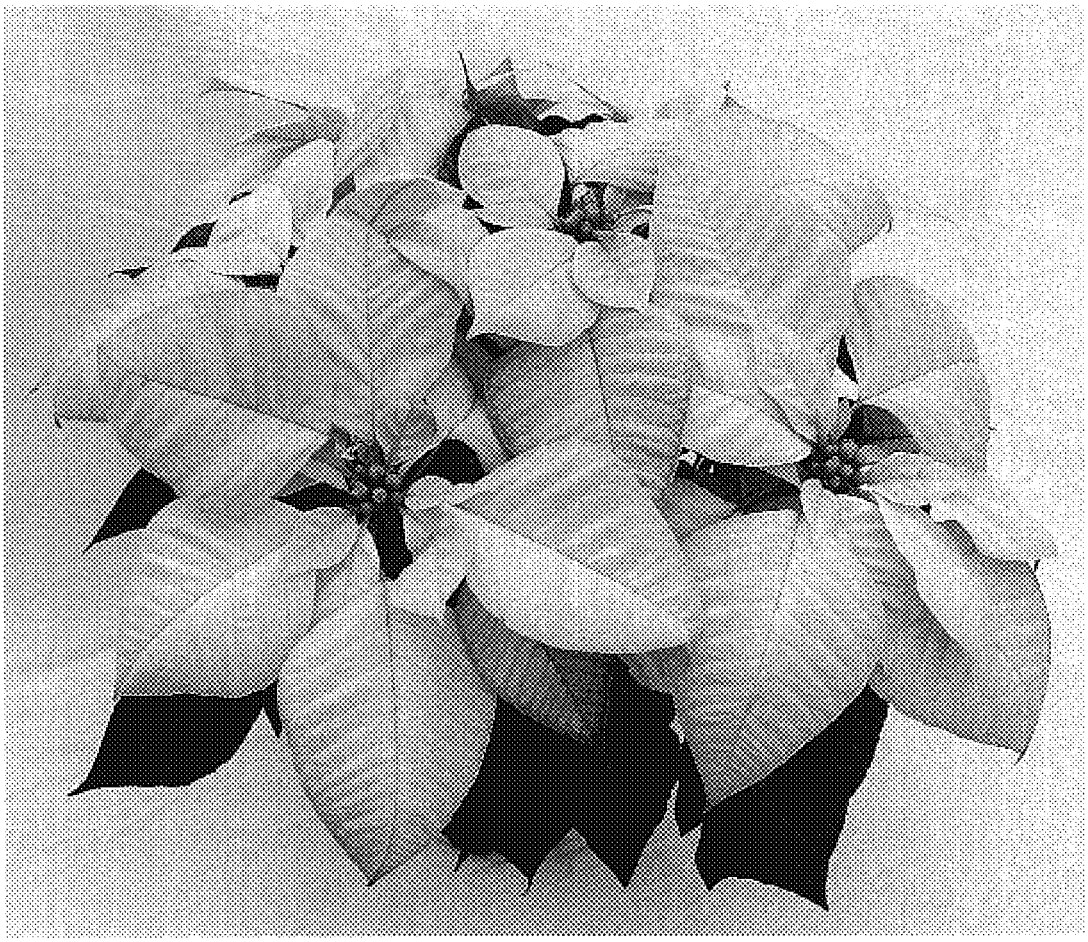

* * * * *